US009045421B2

(12) United States Patent
Gelb et al.

(10) Patent No.: US 9,045,421 B2
(45) Date of Patent: Jun. 2, 2015

(54) REAGENT AND METHOD FOR DETECTION OF CARBOXYLIC ACIDS BY MASS SPECTROMETRY

(75) Inventors: Michael H. Gelb, Seattle, WA (US); Frantisek Turecek, Seattle, WA (US); James Bollinger, Seattle, WA (US)

(73) Assignee: University of Washington, Seattle, WA (US)

( * ) Notice: Subject to any disclaimer, the term of this patent is extended or adjusted under 35 U.S.C. 154(b) by 888 days.

(21) Appl. No.: 13/078,652

(22) Filed: Apr. 1, 2011

(65) Prior Publication Data
US 2011/0294153 A1 Dec. 1, 2011

Related U.S. Application Data

(60) Provisional application No. 61/349,093, filed on May 27, 2010.

(51) Int. Cl.
| | | |
|---|---|---|
| C07D 211/70 | (2006.01) |
| C07D 211/82 | (2006.01) |
| C07D 213/00 | (2006.01) |
| C07D 211/92 | (2006.01) |
| C07D 213/18 | (2006.01) |
| C07D 213/20 | (2006.01) |
| G01N 33/88 | (2006.01) |
| G01N 33/92 | (2006.01) |
| H01J 49/16 | (2006.01) |

(52) U.S. Cl.
CPC .............. *C07D 213/20* (2013.01); *G01N 33/88* (2013.01); *G01N 33/92* (2013.01); *H01J 49/165* (2013.01)

(58) Field of Classification Search
None
See application file for complete search history.

(56) References Cited

U.S. PATENT DOCUMENTS

| | | | | |
|---|---|---|---|---|
| 6,407,220 B1 * | 6/2002 | Huang et al. | 534/618 |
| 7,553,615 B2 * | 6/2009 | Heindl et al. | 435/4 |
| 2010/0022731 A1 * | 1/2010 | Ryan et al. | 526/263 |

OTHER PUBLICATIONS

Eom, SH. et al. Crystallization and Preliminary X-Ray Crystallographic Studies of Rattus norvegicus Visfatin/PBEF/Nampt in Complex with an FK866-Based Inhibitor. Bull. Korean Chem. Soc. 2009, vol. 30, p. 959.*
Elguero, J. et al. Proton, Carbon-13, and Fluorine-19 NMR Study of N-Arylpyridinium Salts: Attempted Calculations of the σI and σ0R Values for N-Pyridinium Substituents. Collection Czechoslovak Chem. Commun. 1981, vol. 46, p. 584.*
Carey, FA. Organic Chemistry 6th Ed. McGraw Hill. 2006, chapter 1, p. 9.*
Barry, S.J., et al., "Derivatisation for Liquid Chromatography/ Electrospray Mass Spectrometry: Synthesis of Pyridinium Compounds and Their Amine and Carboxylic Acid Derivatives," Rapid Communications in Mass Spectrometry 17(6):603-620, Mar. 2003.
Christie, W.W., et al., "Mass Spectrometry of the 4,4-Dimethyloxazoline Derivatives of Isomeric Octadecenoates (Monoenes)," European Journal of Lipid Science and Technology 102(1):23-29, Jan. 2000.
Destaillats, F., and P. Angers, "One-Step Methodology for the Synthesis of FA Picolinyl Esters From Intact Lipids," Journal of the American Oil Chemists' Society 79(3):253-256, Mar. 2002.
Dubois, N., et al., "Convenient Preparation of Picolinyl Derivatives From Fatty Acid Esters," European Journal of Lipid Science and Technology 108(1)28-32, Jan. 2006.
Fay, L., and U. Richli, "Location of Double Bonds in Polyunsaturated Fatty Acids by Gas Chromatography—Mass Spectrometry After 4,4-Dimethyloxazoline Derivatization," Journal of Chromatography A 541:89-98, 1991.
Hamilton, J.T.G., and W.W. Christie, "Mechanisms for Ion Formation During the Electron Impact-Mass Spectrometry of Picolinyl Ester and 4,4-Dimethyloxazoline Derivatives of Fatty Acids," Chemistry and Physics of Lipids 105(1):93-104, Mar. 2000.
Lamos, S.M., et al., "Relative Quantification of Carboxylic Acid Metabolites by Liquid Chromatography—Mass Spectrometry Using Isotopic Variants of Cholamine," Analytical Chemistry 79(14):5143-5149, Jul. 2007.

(Continued)

*Primary Examiner* — Rita Desai
*Assistant Examiner* — Ben S Michelson
(74) *Attorney, Agent, or Firm* — Christensen O'Connor Johnson Kindness PLLC

(57) ABSTRACT

Method and reagent for converting a carboxylic acid to a positively charge amide are described. The method and reagent facilitate positive ion mass spectral analysis of carboxylic acids. The method includes reacting a carboxylic acid with a compound having formula I:

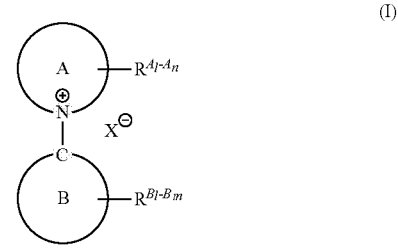

wherein A and B are aromatic rings, ring A includes a quaternized nitrogen and has n additional ring atoms, each additional ring atom optionally substituted with an $R^A$ group, and n is an integer from 4 to 10, and ring B includes a carbon atom and has m additional ring atoms, each additional ring atom optionally substituted with an $R^B$ group, and m is an integer from 4 to 10. The compound includes at least one $R^A$ or $R^B$ group, and the at least one $R^A$ and $R^B$ group is -L-N(Z)H; and $X^-$ is a counterion.

12 Claims, 10 Drawing Sheets

(56) References Cited

OTHER PUBLICATIONS

Tsukamoto, Y., et al., "Synthesis of Benzofurazan Derivatization Reagents for Carboxylic Acids and Its Application to Analysis of Fatty Acids in Rat Plasma by High-Performance Liquid Chromatography—Electrospray Ionization Mass Spectrometry," Biomedical Chromatography 19(10):802-808, Dec. 2005.

Wolff, R.L., et al., "Arachidonic, Eicosapentaenoic, and Biosynthetically Related Fatty Acids in the Seed Lipids From a Primitive Gymnosperm, *Agathis robusta*," Lipids 34(10):1083-1097, Oct. 1999.

Zhuang, W., et al., "Mass Spectrometric Elucidation of Chlorine Location in Dichloro Fatty Acids Following 4,4-Dimethyloxazoline Derivatization, and Its Application to Chlorinated Fatty Acids in Fish," International Journal of Mass Spectrometry 232(2):127-137, Mar. 2004.

\* cited by examiner

REAGENT AND METHOD FOR DETECTION OF CARBOXYLIC ACIDS BY MASS SPECTROMETRY

CROSS-REFERENCE TO RELATED APPLICATION

This application claims the benefit of U.S. Provisional Patent Application No. 61/349,093, filed May 27, 2010, expressly incorporated herein by reference in its entirety.

STATEMENT OF GOVERNMENT LICENSE RIGHTS

This invention was made with Government support under Contract No. 5R37HL036235 awarded by the National Institutes of Health. The Government has certain rights in the invention.

BACKGROUND OF THE INVENTION

Liquid chromatography coupled to electrospray ionization tandem mass spectrometry (LC/ESI-MSMS) has emerged as a powerful method to detect oxygenated derivatives of fatty acids including eicosanoids. With these methods it is possible to analyze a large collection of eicosanoids in a single LC/ESI-MSMS run. These lipid mediators are detected by multiple reaction monitoring in which parent ions are isolated in the first stage of the mass spectrometer followed by collision-induced dissociation to give fragment ions, which are detected after an additional stage of mass spectrometer isolation. The current limit of quantification of analytes is in the 10-20 pg range. This sensitivity level is appropriate for studies with cultured cells in vitro or with relatively large tissue samples, but it is not sufficient for studies with smaller volume samples such as joint synovial fluid or bronchoalveolar lavage fluid from experimental rodents.

For reasons that are not well understood, cations generally form gaseous ions better than anions in the electrospray ionization source of the mass spectrometer. Additionally, for underivatized carboxylic acids it is required to add a weak organic acid to the chromatographic mobile phase (e.g., formic acid) so that the carboxylic acid is kept in its protonated state, which allows it to be retained on the reverse-phase column to ensure chromatographic separation. However, the presence of the weak acid offsets the formation of carboxylate anions in the electrospray source because the weak acid carries most of the anionic charge in the electrospray droplets, and thus formation of analyte anions is suppressed.

However, despite the attractiveness of converting the carboxylic acid to a fixed charge cationic derivative, organic cations tend to fragment by collision-induced dissociation near the cationic site. Fragmentation in the derivatization tag is not desirable because analytes that form isobaric parent ions and that co-migrate on the LC column will not be distinguished in the mass spectrometer if they give rise to the same detected fragment ion. This loss of analytical specificity is a serious problem when analyzing complex biological samples. Fragmentation in the analyte portion rather than in the tag portion also reduces chemical noise, which also enhances sensitivity of detection.

Given the importance of oxygenated fatty acid derivatives in numerous medically important processes such as inflammation and resolution of inflammation, a need exists to improve the LC/ESI-MSMS sensitivity of detection of these lipid mediators using a widely available analytical platform. The present invention seeks to fulfill this need and provide further related advantages.

SUMMARY OF THE INVENTION

In one aspect, the invention provides a method for derivatizing a carboxylic acid. In one embodiment, the method comprises reacting a carboxylic acid with a quaternary ammonium reagent having a permanent positive charge to provide an amide having a permanent positive charge, wherein the quaternary ammonium reagent has the formula

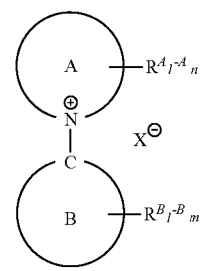

wherein A and B are aromatic rings, ring A includes a quaternized nitrogen and has n additional ring atoms, each optionally substituted with an $R^A$ group, and n is an integer from 4 to 10, and ring B includes a carbon atom and has m additional ring atoms, each optionally substituted with an $R^B$ group, and m is an integer from 4 to 10, wherein the reagent includes at least one $R^A$ or $R^B$ group, and wherein the at least one $R^A$ and $R^B$ group is -L-N(Z)H, wherein L is an optional linker moiety including from one to twenty atoms, and Z is hydrogen, an alkyl group including from one to twenty carbon atoms, or an aryl group including from five to ten carbon atoms; and $X^-$ is a counterion.

In another aspect, the invention provides a method for measuring the mass spectrum of a carboxylic acid derivative. In one embodiment, the method comprises:

(a) preparing an amide derivative having a permanent positive charge from a carboxylic acid by reacting the carboxylic acid with an quaternary ammonium reagent having a permanent positive charge, wherein the quaternary ammonium reagent has the formula

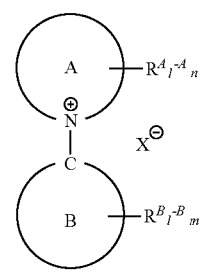

wherein A and B are aromatic rings, ring A includes a quaternized nitrogen and has n additional ring atoms, each optionally substituted with an $R^A$ group, and n is an integer from 4 to 10, and ring B includes a carbon atom and has m additional ring atoms, each optionally substituted with an $R^B$ group, and m is an integer from 4 to 10, wherein the reagent includes at least one $R^A$ or $R^B$ group, and wherein the at least one $R^A$ and $R^B$ group is -L-N(Z)H, wherein L is an optional linker moiety including from one to twenty atoms, and Z is hydrogen, an alkyl group including from one to twenty carbon atoms, or an aryl group including from five to ten carbon atoms; and $X^-$ is a counterion; and (b) measuring the mass spectrum of the amide derivative having a permanent positive charge.

In one embodiment, measuring the mass spectrum comprises measuring the mass spectrum by electrospray ionization mass spectrometry. In one embodiment, measuring the mass spectrum comprises measuring the mass spectrum by positive ion mode electrospray ionization mass spectrometry.

In another aspect, the invention provides a method for detecting a carboxylic acid in a sample. In one embodiment, the method comprises:

(a) treating a sample with a quaternary ammonium reagent having a permanent positive charge under reaction conditions sufficient to form an amide derivative having a permanent positive charge from a carboxylic acid present in the sample to provide a treated sample, wherein the quaternary ammonium reagent has the formula

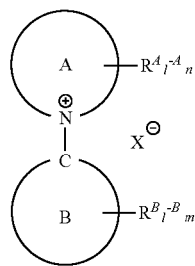

wherein A and B are aromatic rings, ring A includes a quaternized nitrogen and has n additional ring atoms, each optionally substituted with an $R^A$ group, and n is an integer from 4 to 10, and ring B includes a carbon atom and has m additional ring atoms, each optionally substituted with an $R^B$ group, and m is an integer from 4 to 10, wherein the reagent includes at least one $R^A$ or $R^B$ group, and wherein the at least one $R^A$ and $R^B$ group is -L-N(Z)H, wherein L is an optional linker moiety including from one to twenty atoms, and Z is hydrogen, an alkyl group including from one to twenty carbon atoms, or an aryl group including from five to ten carbon atoms; and $X^-$ is a counterion; and (b) subjecting the treated sample to mass spectrometric analysis to determine the presence of the amide derivative having a permanent positive charge, wherein the presence of the amide derivative is indicative of the presence of a carboxylic acid in the sample.

In one embodiment, the method further comprises identifying the carboxylic acid by analyzing the mass spectrum of the amide derivative. In one embodiment, subjecting the treated sample to mass spectrometric analysis comprises measuring the mass spectrum by electrospray ionization mass spectrometry. In one embodiment, subjecting the treated sample to mass spectrometric analysis comprises measuring the mass spectrum by positive ion mode electrospray ionization mass spectrometry.

In another aspect, the invention provides a kit for derivatizing a carboxylic acid. In one embodiment, the kit comprises:

(a) a container comprising a quaternary ammonium reagent having the formula

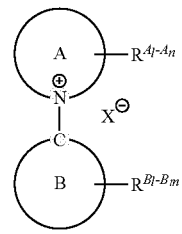

wherein A and B are aromatic rings, ring A includes a quaternized nitrogen and has n additional ring atoms, each optionally substituted with an $R^A$ group, and n is an integer from 4 to 10, and ring B includes a carbon atom and has m additional ring atoms, each optionally substituted with an $R^B$ group, and m is an integer from 4 to 10, wherein the reagent includes at least one $R^A$ or $R^B$ group, and wherein the at least one $R^A$ and $R^B$ group is -L-N(Z)H, wherein L is an optional linker moiety including from one to twenty atoms, and Z is hydrogen, an alkyl group including from one to twenty carbon atoms, or an aryl group including from five to ten carbon atoms; and $X^-$ is a counterion; and (b) indicia providing instructions for using the quaternary ammonium reagent to derivatize a carboxylic acid.

In certain embodiments of the above methods and kit, the quaternary ammonium reagent has the formula

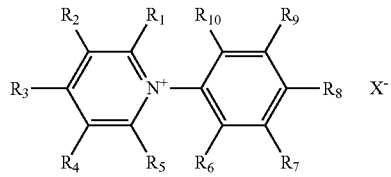

wherein $R_1$-$R_{10}$ are independently selected from hydrogen and groups having from one to ten atoms, wherein at least one of $R_1$-$R_{10}$ is -L-N(Z)H, wherein L is an optional linker moiety including from one to twenty atoms, Z is hydrogen, an alkyl group including from one to twenty carbon atoms, or an aryl group including from five to ten carbon atoms, and X is a counterion. In one embodiment, the quaternary ammonium reagent is an N-(4-aminomethylphenyl)pyridinium (AMPP) salt.

In another aspect of the invention, a reagent for derivatizing carboxylic acids is provided. In one embodiment, the reagent has the formula

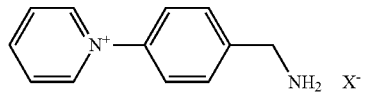

wherein $X^-$ is a stable anion. Salts of the reagent (e.g., protonated amine forms) are also provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A, early eluting eicosanoids; and FIG. 3B, later eluting eicosanoids.

DETAILED DESCRIPTION OF THE INVENTION

Figure 1:
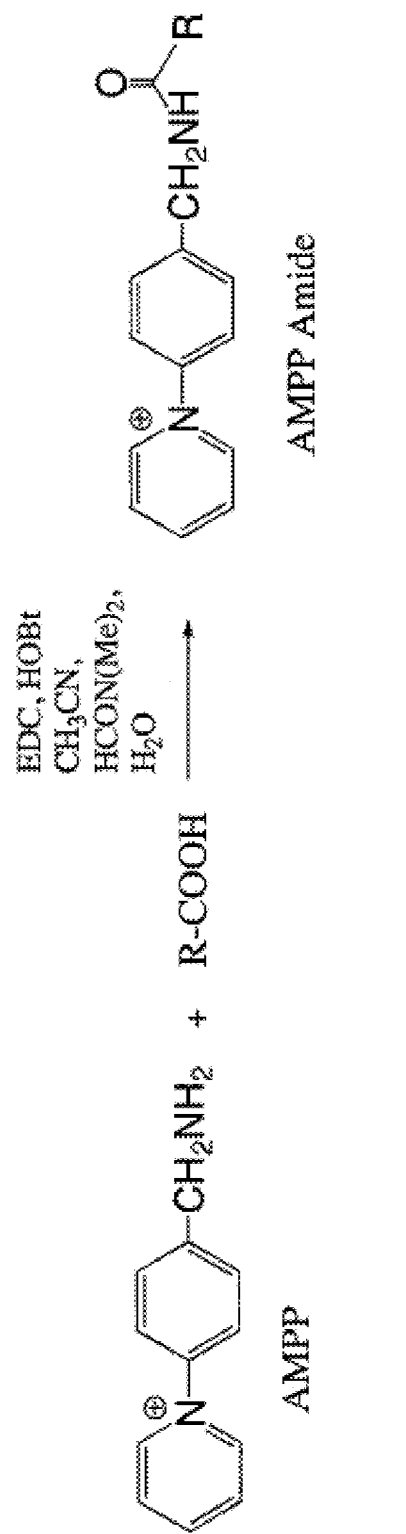
FIG. 1 illustrates the use of a representative reagent of the invention, AMPP, to derivatize a representative carboxylic acid, R—COOH, to provide an AMPP amide (reagents for derivatization are shown).

The present invention provides a method and reagent for converting a carboxylic acid to a positively charged amide. The reagent is a quaternary ammonium compound that includes an amine group. The amine group reacts with a carboxylic acid's carboxyl group to provide an amide and the quaternary ammonium group imparts a permanent positive charge to the amide. The method and reagent facilitate positive ion mass spectral analysis of carboxylic acids. The reagent provides a positively charged amide that, in positive ion mass spectrometry, preferably fragments in the parent carboxylic acid portion of the amide and does not fragment in the tag (i.e., the portion of the amide derived from the reagent).

The reagent useful in the method of the invention is a quaternary ammonium compound having a permanent positive charge and reacts with a compound having one or more carboxylic acid groups to provide an amide derivative having a permanent positive charge. As used herein, the term "permanent positive charge" refers to a compound having a permanent positively charged nitrogen atom (i.e., a nitrogen atom that is not protonated). The reagent useful in the method of the invention or the product formed from the reagent each have a permanent positive charge (i.e., a quaternary nitrogen center).

The reagent useful in the method of the invention has formula I:

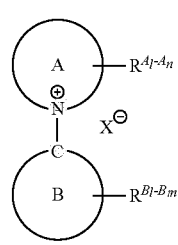

I wherein A and B are aromatic rings, ring A includes a quaternized nitrogen and has n additional ring atoms, each optionally substituted with an $R^A$ group (i.e., up to n $R^A$ groups, for example, from $R^{A1}$ to $R^{An}$), and n is an integer from 4 to 10, and ring B includes a carbon atom bonded to the quaternized nitrogen of ring A and has m additional ring atoms, each optionally substituted an $R^B$ group (i.e., up to m $R^B$ groups, for example, from $R^{B1}$ to $R^{Bm}$), and m is an integer from 4 to 10, wherein the reagent includes at least one $R^A$ or $R^B$ group, and wherein at least one of $R^A$ or $R^B$ group is -L-N(Z)H, wherein L is an optional linker moiety including from one to twenty atoms, and Z is hydrogen, an alkyl group including from one to twenty carbon atoms, or an aryl group including from five to ten carbon atoms; and X is a counterion.

In formula I, aromatic ring A is covalently coupled to aromatic ring B through a single bond between the quaternized nitrogen of ring A and a carbon atom of ring B. In addition to the quaternized nitrogen, ring A can include one or more heteroatoms (e.g., N, O, S, Si, P), and ring B can include one or more heteroatoms (e.g., N, O, S, Si, P). Thus, ring A is a heteroaromatic ring and ring B can be a heteroaromatic ring. Representative heteroaromatic rings include pyridyl, furanyl, thiophenyl, pyrazinyl, pyrazolyl, imidazolyl, thiazolyl, oxazolyl, and isoxazolyl rings, and representative aromatic rings include phenyl and naphthyl.

In addition to the quaternized nitrogen, ring A can include up to n ring atoms, each optionally substituted with an $R^A$ group, and ring B, in addition to the carbon atom coupled to ring A through a single bond, can include up to m ring atoms, each optionally substituted with an $R^B$ group. Representative reagents of the invention have n from 4-10 and m from 4-10. In certain embodiments, n is 4 or 5 and m is 4 or 5. In one embodiment, n=4 and m=4. In one embodiment, n=4 and m=5. In one embodiment, n=5 and m=4. In one embodiment, n=5 and m=5. In one embodiment, ring A is pyridyl and ring B is phenyl.

Groups $R^A$ and $R^B$ are independently selected from groups having from one to ten atoms. Representative groups $R^A$ and $R^B$ include alkyl and aryl groups that may include one or more heteroatoms (e.g., methyl or methoxy, phenyl or methoxyphenyl). The reagent of formula (I) includes at least one $R^A$ or $R^B$ group, and at least one of these $R^A$ or $R^B$ groups is -L-N(Z)H. L is an optional linker moiety including from one to twenty atoms (e.g., an alkylene or arylene group that may further include one or more heteroatoms (e.g., methylene, phenylene), and Z is hydrogen, an alkyl group including from one to twenty carbon atoms, or an aryl group including from five to ten carbon atoms. In one embodiment, L is methylene (—$CH_2$—) and Z is hydrogen. In one embodiment, the reagent of formula I includes a single -L-N(Z)H group.

The reagent useful in the invention is a quaternary ammonium compound that includes a counterion ($X^-$). Suitable counterions include stable anions. Suitable counterions include the counterions that result from the initial synthesis of the compound. Suitable counterions ions also include those exchanged with the counterion ion provided by the initial synthesis. Representative counterions include chloride, bromide, fluoride, iodide, formate, acetate, and trifluoroacetate, among others.

In one embodiment, the reagent useful in the method has formula II:

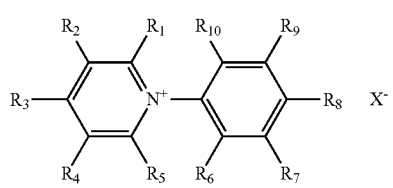

II wherein $R_1$-$R_{10}$ are independently selected from hydrogen and groups having from one to ten atoms (e.g., an alkyl or aryl group that may further include one or more heteroatoms), wherein at least one of $R_1$-$R_{10}$ is -L-N(Z)H, wherein L, Z, and X are as described above for the reagent of formula I. In one embodiment, formula (II) includes a single -L-N(Z)H group. In one embodiment, $R_1$-$R_7$, $R_9$, and $R_{10}$, are hydrogen, and $R_8$ is -L-N(Z)H. In one embodiment, L is methylene (—$CH_2$—) and Z is hydrogen.

In one embodiment, the reagent useful in the method is an N-(4-aminomethylphenyl)pyridinium (AMPP) salt (e.g., AMPP chloride, AMPP trifluoroacetate). AMPP has the structure:

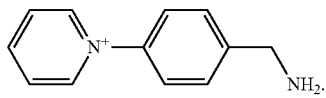

The reagent of the invention includes an amine group and it will be appreciated that, depending on the reagent's environment, the reagent can be in the form of a free amine (i.e., —$NH_2$) or its salt (i.e., protonated form, —$NH_3^+$).

In one aspect, the invention provides a method for converting a carboxylic acid to a positively charged amide using the reagent of formula I. By virtue of the reagent's amine group, the reagent readily reacts with a carboxylic acid to provide an amide derivative in high yield. The derivatization of a representative carboxylic acid ($RCO_2H$) with a representative reagent of formula II is illustrated in Scheme 1.

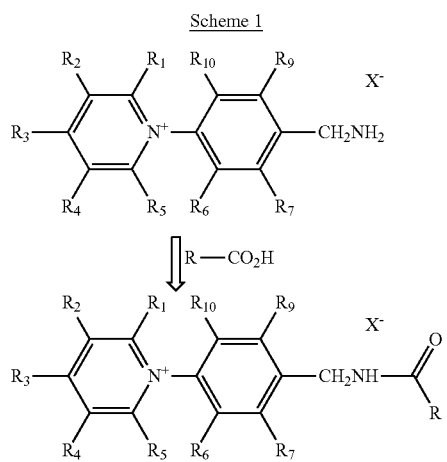

The derivatization of a representative carboxylic acid ($RCO_2H$) with AMPP is illustrated in Scheme 2.

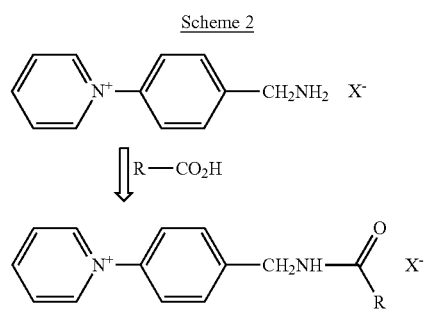

As noted above, the reagent useful in the method of the invention is a quaternary ammonium compound having a permanent positive charge and reacts with a compound having one or more carboxylic acid groups to provide an amide derivative having a permanent positive charge. Carboxylic acids that can be advantageously derivatized by the reagents in the methods of the invention include carboxylic acid-containing therapeutic drugs, carboxylic acid-containing therapeutic drug candidates, and carboxylic acid-containing metabolites (e.g., pyruvates). Other examples of carboxylic acids that can be advantageously derivatized by the reagents in methods of the invention include fatty acids, prostaglandins, eicosanoids, and their metabolites. Tetrahydrocannabinol (THC), its isomers, and its metabolites can also be derivatized by the reagent and analyzed by the methods of the invention. The carboxylic acid can be from a biological sample. Examples of biological samples include serum, urine, bronchoalveolar lavage fluid, cell lysates, and tissue homogenates.

Design and Preparation of AMPP Amides.

Figure 4:
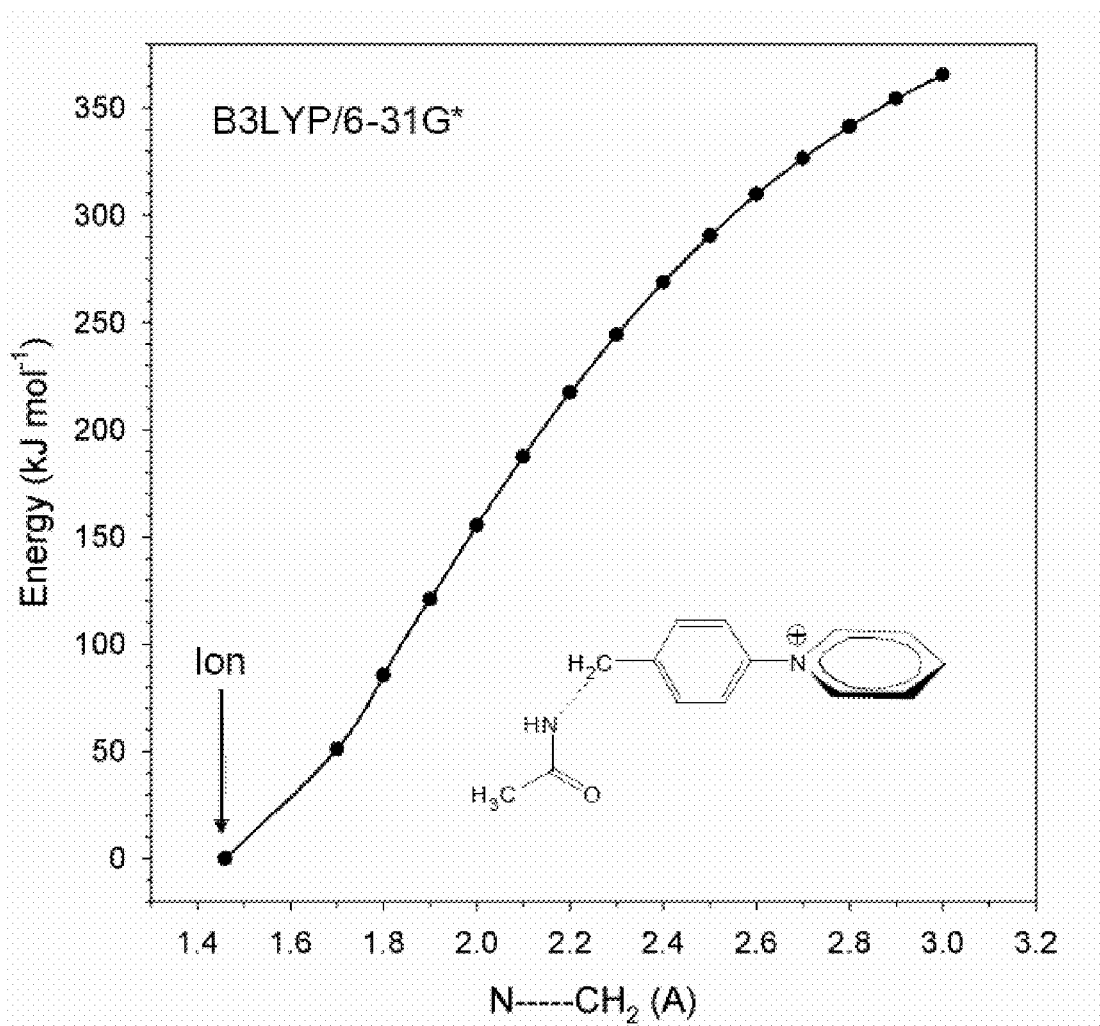
FIG. 4 is the B3LYP/6-31G* calculated potential energy profile for the N—$CH_2$ benzylic bond dissociation for a representative charge tag, AMPP.

The present invention provides a simple derivatization procedure to convert the carboxylic acid terminus of eicosanoids to a cationic group so that mass spectrometry can be carried out in positive mode. The tag was designed so that fragmentation occurs in the analyte portion rather than in the tag portion so that the power of tandem mass spectrometry was used for analytical specificity and sensitivity. Computational analysis of substituted N-pyridinium methylamino derivatives indicated that these had only moderate dissociation energies for loss of pyridine and other single bond cleavages in the linker, and thus might not be suitable, which require fragmentation in the fatty acyl chain. Therefore, the charge tag was redesigned to strengthen the pyridinium N—C bond by inserting a phenyl ring as a linker. The phenyl ring also serves to enhance the derivative's interaction with the reverse phase column, which is used as a sample clean-up step prior to LC/ESI-MSMS. Density functional theory calculations (B3LYP/6-31G*) indicated that homolytic cleavage of the benzylic $CH_2$—N bond in the charge tag was a high-energy process that required >350 kJ $mol^{-1}$ of dissociation energy and was deemed not to out compete fragmentations in the fatty acyl chain (FIG. 4). A side reaction that could not be evaluated using the model system shown in FIG. 4 is elimination of 4-(N-pyridyl)benzylamine, which gives rise to the m/z 183 marker fragment ion. An amide linkage of the charge tag to the analytic carboxylic acid was preferred over an ester because the former are generally more resistant to fragmentation in the mass spectrometer. The final feature of the design of representative reagent AMPP is its ease of synthesis in pure form.

In one aspect, the invention provides the synthesis of highly pure N-(4-aminomethylphenyl)pyridinium (AMPP, FIG. 1) salt, a new derivatization reagent. A method was developed to convert the carboxyl group of lipid mediators to the AMPP amide using a carbodiimide coupling reagent. Coupling conditions were optimized to give near quantitative formation of the AMPP amide. The versatility and effectiveness of the reagent is shown by converting the fluorescent fatty acid 10-pyrene-decanoic acid into its AMPP amide and examining the reaction mixture by fluorimetric HPLC and ESI-MS. No remaining 10-pyrenedecanoic acid was detected, and the AMPP amide was formed in >95% yield with <1% N-acyl urea formation (a common side product in carbodiimide-promoted couplings). Derivatization was carried out using a single reagent cocktail in a small vial heated at 60° C. for 30 min without the need for anhydrous or anaerobic conditions.

LC/ESI-MSMS Analysis of Eicosanoid AMPP Amides.

Figure 2A:
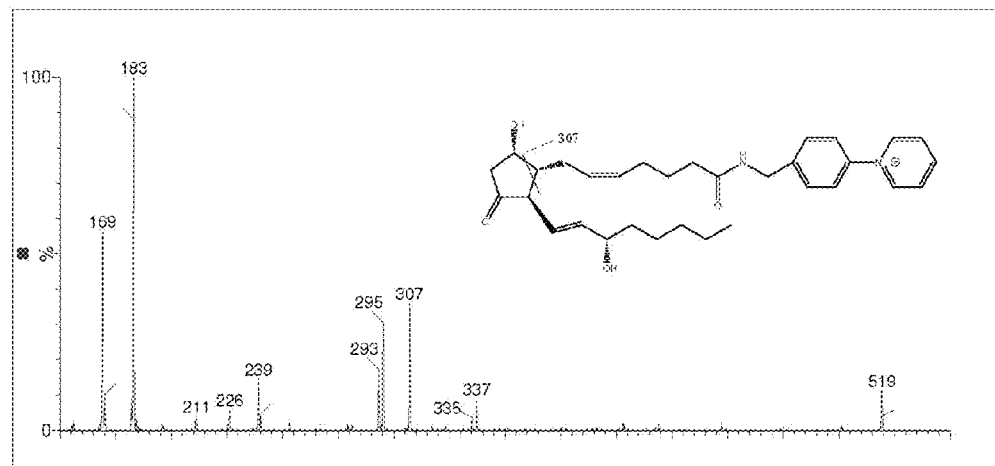
FIGS. 2A-2L are fragment ion spectra of representative eicosanoid AMPP amides: $PGD_2$ (2A), $PGE_2$ (2B), $PGF_{2\alpha}$ (2C), arachidonic acid (2D), $TxB_2$ (2E), 6-keto-$PGF_{1\alpha}$ (2F), 5(S)-HETE (2G), 8(S)-HETE (2H), 11(S)-HETE (2I), $LTB_4$ (2J), 12(S)-HETE (2K), and 15(S)-HETE (2L).
Figure 2B:
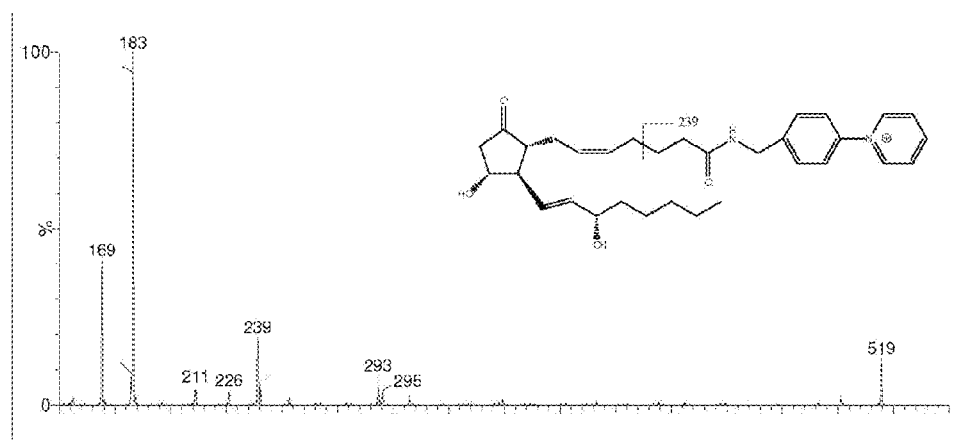
Figure 2C:
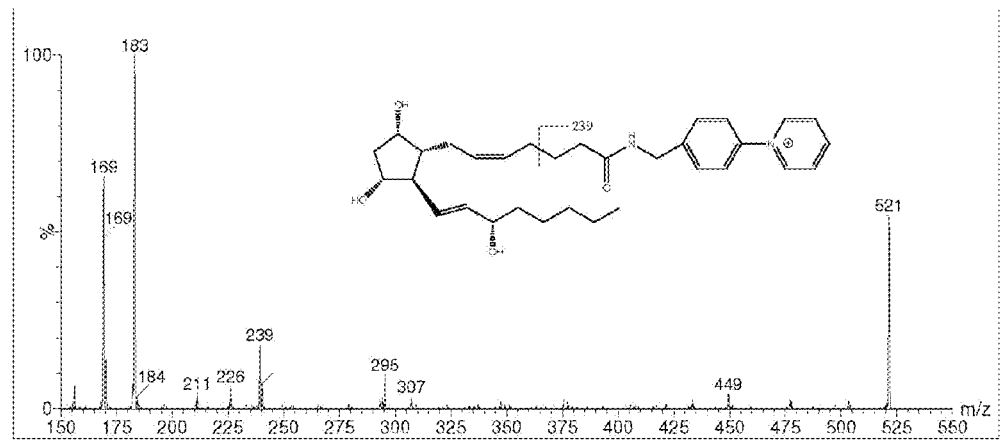
Figure 2D:
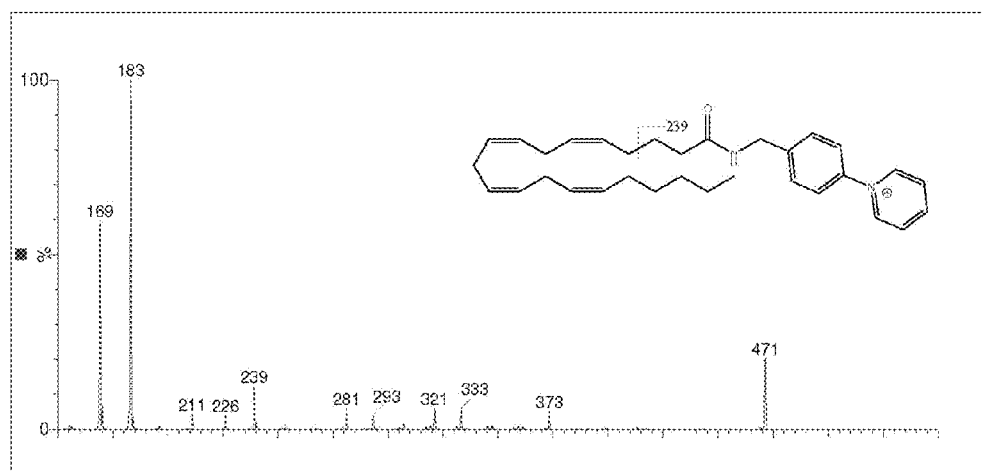
Figure 2E:
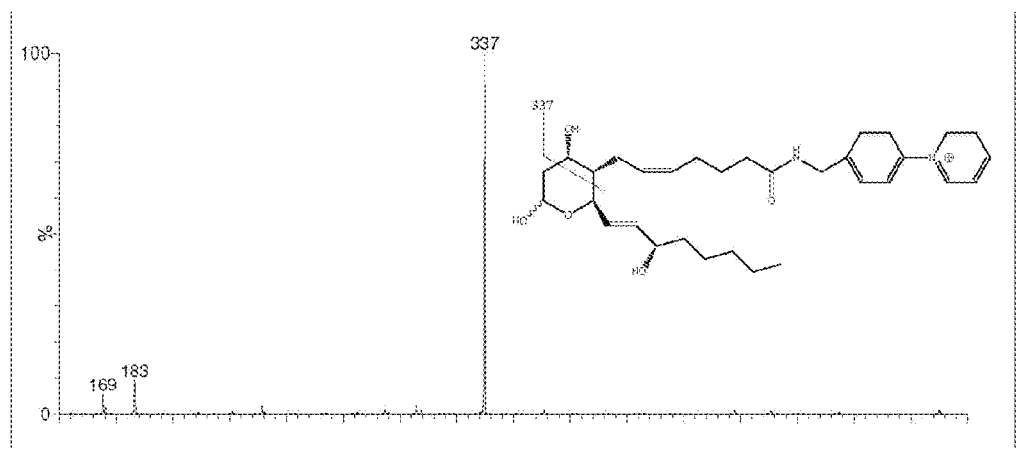
Figure 2F:
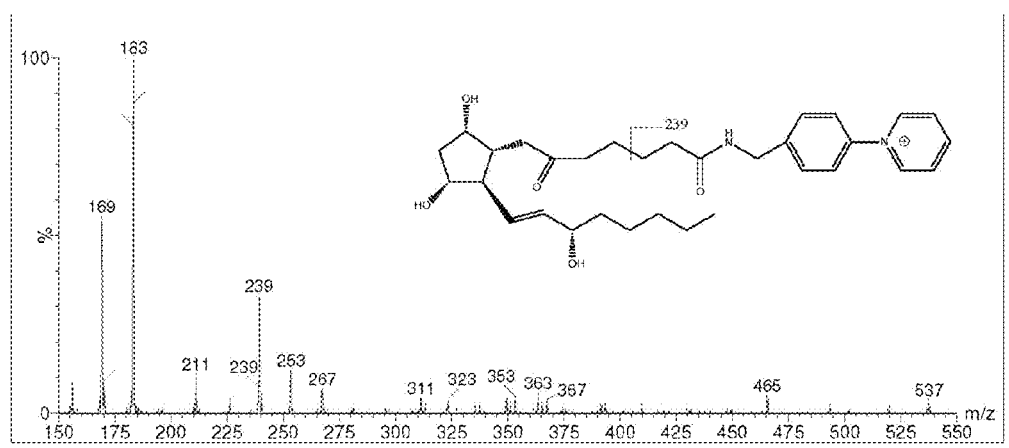
Figure 2G:
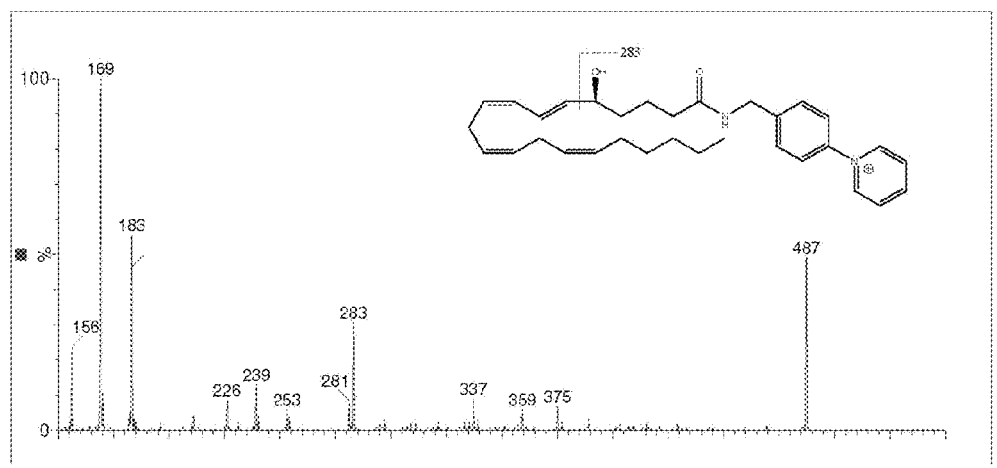
Figure 2H:
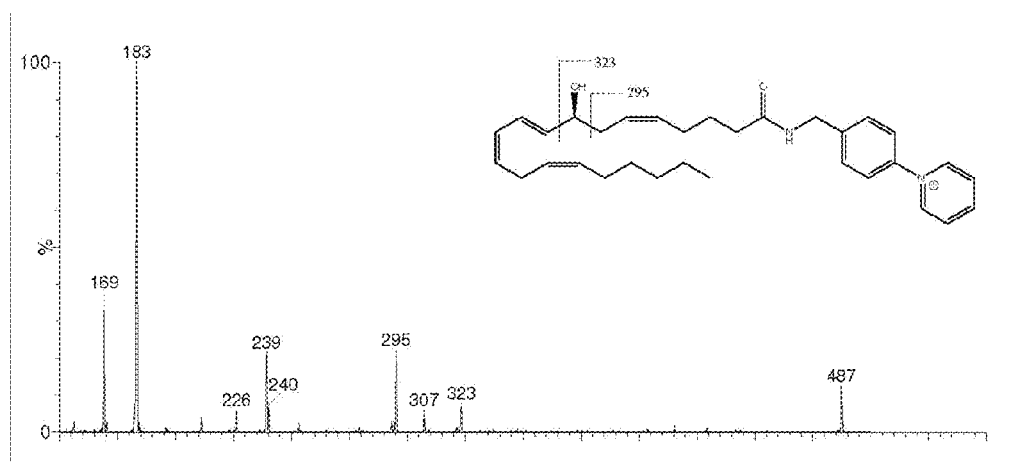
Figure 2I:
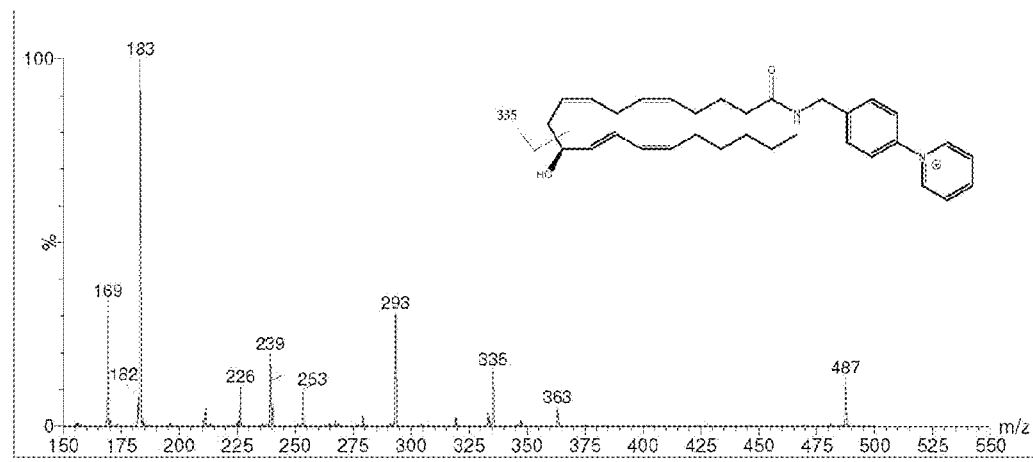
Figure 2J:
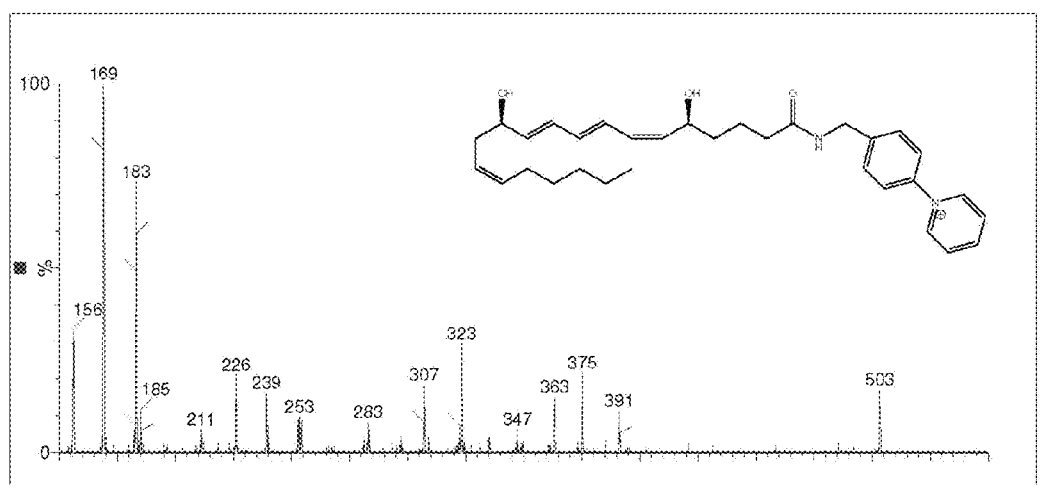
Figure 2K:
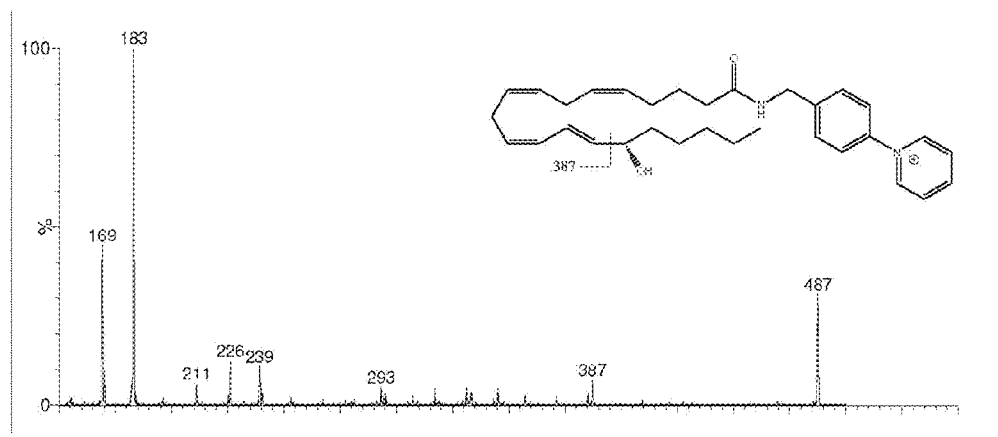
Figure 2L:
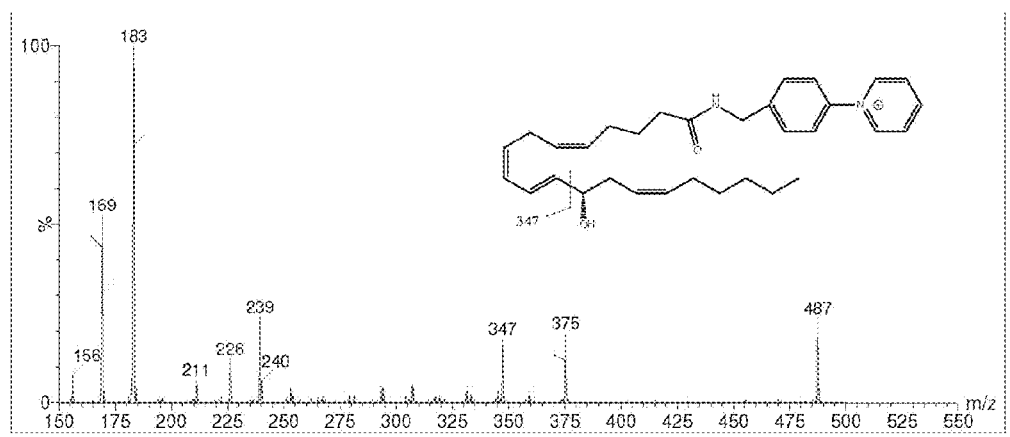

The analytes studied were $PGD_2$, $PGE_2$ and $PGF_{2\alpha}$, 6-keto-$PGF_{1\alpha}$ (the spontaneous breakdown product from prostacyclin, $PGI_2$), $TxB_2$ (the spontaneous breakdown product from $TxA_2$), $LTB_4$, 5(S)-HETE), 8(S)-HETE, 11(S)-HETE, 12(S)-HETE and 15(S)-HETE, and arachidonic acid. ESI-MSMS analysis with fragment ion scanning of AMPP amides of the analytes are shown in FIGS. 2A-2L. In all spectra, some cleavage of the AMPP tag occurs giving rise to the peaks at m/z=169 and 183. To best ensure analytical specificity, the eicosanoids were quantified using a fragment in the analyte portion rather than in the AMPP tag. For $PGD_2$, the m/z=307 fragment, which is likely due to cross-ring cleavage of the cyclopentanone ring was used and represents the most abundant non-tag fragment ion (FIG. 2A). For $PGE_2$ and $PGF_{2\alpha}$, m/z=239 was used due to cleavage between C3 and C4 (FIGS. 2B and 2C, respectively). For arachidonic acid and 6-keto-$PGF_{1\alpha}$, m/z=239 was used, again due to C3-C4 cleavage (FIGS. 2D and 2F, respectively). The major non-tag fragment for $TxB_2$ is m/z=337 due to cross-ring cleavage (FIG. 2E). For all HETE species, a unique fragment ion (see Table 1) was identified to avoid cross contamination of MSMS signals due to partially unresolved LC peaks (FIGS. 2G-2L). Finally, for $LTB_4$, m/z=323 was used, which is the most abundant non-tag fragment ion but has a non-obvious origin.

A mixture of eicosanoids in phosphate buffered saline was evaluated and optimized pre-ESI-MSMS sample workup and LC/ESI-MSMS conditions. Critical for a successful method with ultra-sensitive analyte detection is high yield recovery of analytes from the sample prior to LC/ESI-MSMS analysis. Solid phase extraction with a rapidly wettable matrix (Oasis HLB cartridges, Waters Inc. or Strata-X cartridges, Phenomenex) combined with analyte elution with methanol gave high yield recovery of all eicosanoids analyzed (Table 1). The data in Table 1 is based on 50 pg of each analyte submitted to recovery studies. When the same recovery studies were carried out with 5 pg of eicosanoid, results were essentially identical. Inferior recoveries were obtained using elution of the solid phase cartridges with acidified methanol or if the sample was subjected to liquid-liquid extraction or protein precipitation using various solvents.

Figure 3A:
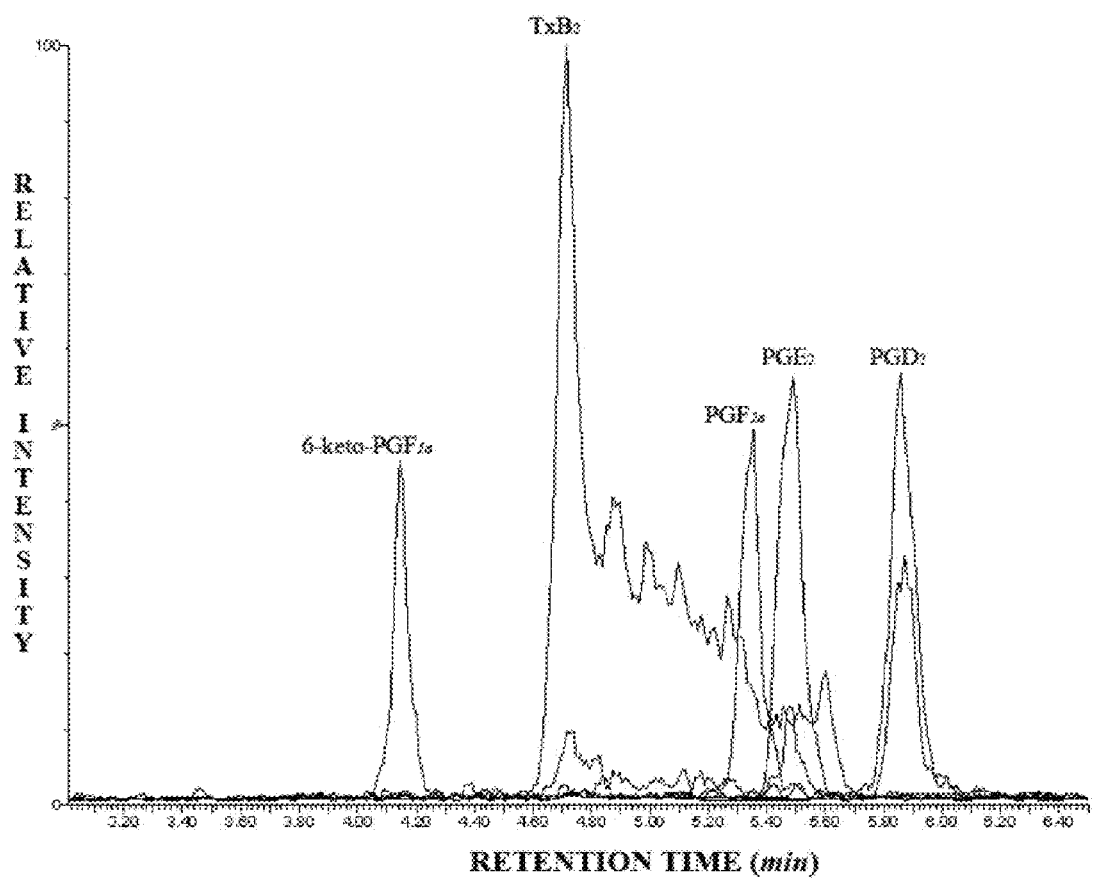
FIGS. 3A and 3B are LC/ESI-MSMS traces of representative eicosanoids after workup from a solution in phosphate buffered saline.
Figure 3B:
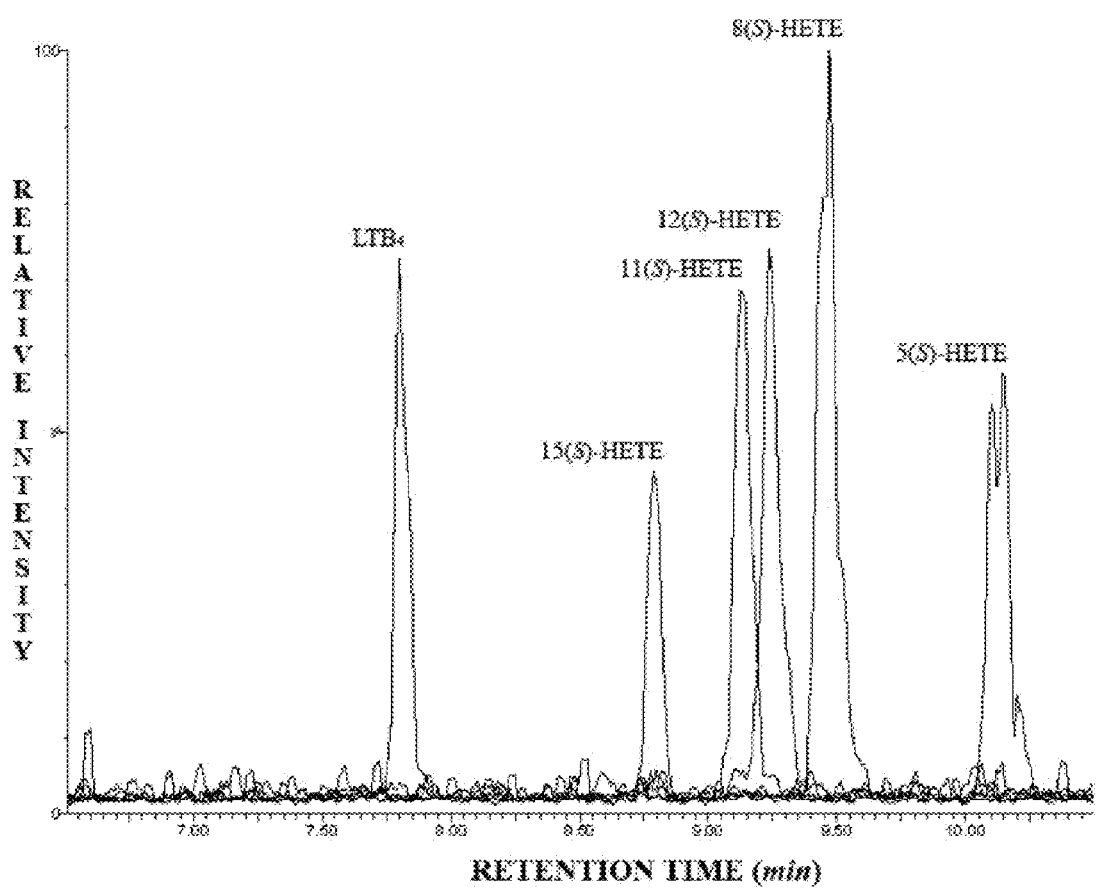

FIGS. 3A and 3B shows typical LC/ESI-MSMS runs of an eicosanoid mixture. All of the analytes examined elute from the LC column in less than 11 min. All HETEs except 11(S)- and 12(S)- are baseline resolved. The partial overlap of 11(S)- and 12(S)-HETEs is not a concern because completely selective fragment ions are being monitored. $TxB_2$ gives rise to the typical broad peak shape due to interconversion between the two hemiacetal isomers. The fragments used to monitor $PGD_2$ and $PGE_2$ (isobars of each other) are not completely unique to each species, but baseline LC resolution of these two eicosanoids solves the issue. The same is true for the isobaric pair $TxB_2$ and 6-keto-$PGF_{1\alpha}$. To ensure high yield conversion of eicosanoids to AMPP amides with minimal formation of N-acyl-ureas, a large excess of derivatization reagents were used. The AMPP tag and the EDCI coupling reagent elute in the void volume and the HOBt elutes in the large time window between $PGD_2$ and $LTB_4$. Thus removal of excess derivatization reagents is not necessary prior to LC/ESI-MSMS.

Standard curve analysis was carried out by mixing various amounts of the analytes with 50 pg of each internal standard. In all cases, the mass spectrometry response was linear from the limit of quantification up to the highest amount analyzed (19 pg on-column for the Waters Quattro Micro and 5-10 pg on-column for the Waters Quattro Premier). Limit of quantification was defined as the amount of eicosanoid AMPP amide needed to give an ESI-MSMS signal that is 10-fold the noise (as determined using the Waters MassLynx software). Limit of quantification for all eicosanoid AMPP amides are listed in Table 1. The values using the Waters Quattro Micro are 5 pg for all eicosanoids except 12(S)-HETE (10 pg) and arachidonic acid (10 pg). With the Waters Quattro Premier the values are 0.2-0.5 pg for all eicosanoids except 12(S)-HETE (0.9 pg) and arachidonic acid (1 pg).

Limit of quantification of underivatized eicosanoids analyzed by LC/ESI-MSMS in negative ion mode was determined. Values are shown in Table 1 for the Waters Quattro Micro and the Waters Quattro Premier. The method using AMPP amides is found to be 10- to 20-fold more sensitive on both instruments, which constitutes a significant improvement in detection sensitivity of eicosanoids.

The reproducibility of the AMPP derivatization method for eicosanoid analysis was evaluated and results are summarized in Table 2. Three repetitive LC/ESI-MSMS analyses of an identical sample (19 pg on-column levels of each eicosanoid) gave coefficients of variation in the range of 2.4 to 12.7% range. Three independent mixtures of eicosanoids (50 pg each) in phosphate buffered saline were prepared, submitted to sample work-up, and analyzed each by LC-ESI-MSMS (19 pg on-column) (Table 2). Coefficients of variation ranged from 2.8 to 28.2%. Three independent serum aliquots (10 μL) were analyzed and the coefficient of variation ranged from 3.7 to 13.7%.

A mixture of eicosanoids present in mouse serum was evaluated to test the AMPP derivatization method on a complex biological sample. Representative LC/ESI-MSMS traces are shown in FIG. 4 for a relatively high abundant serum eicosanoid ($TxB_2$) and a relatively low abundant eicosanoid ($PGF_{2\alpha}$). Eicosanoids levels are shown in Table 3 for multiple runs and with different volumes of serum analyzed. Eicosanoid formation in calcium ionophore stimulated primary bronchial epithelial cells was evaluated. Results are summarized in Table 4.

The present invention provides a derivatization procedure to convert carboxylic acids to AMPP amides that significantly improves the sensitivity for detection of eicosanoids by LC/ESI-MSMS. Antibody-based quantification of eicosanoids have a limit of quantification around 1 pg, and the method requires that each analyte be quantified in a single assay well. Thus, if 12 eicosanoids are to be analyzed, one requires a sample containing about 12 pg of each species. The AMPP amide method disclosed in the current study can detect all 12 eicosanoid species in a single sample containing about 0.3-1 pg of each eicosanoid and is thus more than an order of magnitude more sensitive than antibody based detection. Previously reported LC/ESI-MSMS detection of underivatized eicosanoids in negative ion mode provide limit of quantification in 10 pg range (see also Table 1), and thus the method of the invention is more than an order of magnitude more sensitive than these methods.

Synthesis of AMPP.

Pyridine (40 mmole, 3.2 mL) was dissolved in 46 mL absolute ethanol followed by the addition of 1-chloro-2,4-dinitrobenzene (40 mmole, 8.2 g, Aldrich). The mixture was heated with a reflux condenser at 98° C. for 16 hr under nitrogen. After cooling, ethanol was removed by rotary evaporation, and the crude product was recrystallized by dissolving in a minimal amount of hot ethanol and allowing the solution to cool. The product N-2,4dinitrophenyl pyridinium chloride was isolated as a yellow solid in 62% yield, and its identity was confirmed by melting point analysis (189-191° C. observed, 189-190° C. reported).

N-2,4-Dinitrophenyl pyridinium chloride (16.8 mmoles, 4.76 g) was dissolved in 70 mL of ethanol:pyridine (3:1). 4-[(N-Boc)amino-methyl]aniline (33.6 mmoles, 7.56 g, Aldrich) was added, and the reaction mixture was heated under a reflux condenser at 98° C. under nitrogen for 3 hr. After cooling, 700 mL water was added to precipitate 2,4-dinitroaniline. After filtration, the filtrate was concentrated to dryness by rotary evaporation, and the product was isolated as a brown oil. This oil was treated with 112 mL 25% (v/v) trifluoroacetic acid in dichloromethane for 30 min at room temperature. The mixture was concentrated by rotary evaporation, and the solid was triturated twice with benzene to remove excess trifluoroacetic acid. The mixture was again concentrated by rotary evaporation. The residue was dissolved in a minimal amount of heated ethanol, the solution was allowed to cool for 5 min and then diethyl ether was added with swirling until the solution started to cloud up. The mixture was transferred to the freezer (−20° C.) and left overnight. The mixture was allowed to warm to room temperature and then decanted. The obtained mother liquor was treated with additional diethyl ether as above to give additional AMPP solid. The solids were combined and triturated with diethyl ether. The solid was dried under vacuum to give 3.30 g of AMPP (as its trifluoroacetate) as a brown solid, 59% yield. $^1$H-NMR (300 MHz, $d_6$-DMSO) 9.34 (d, 2H), 8.81 (t, 1H), 8.53 (broad, 3H), 8.33 (t, 2H), 7.95 (d, 2H), 7.80 (d, 2H), 4.22 (s, 2H).

Preparation of Samples Prior to Derivatization with Ampp.

A glass auto-sampler vial insert (Agilent, Cat. 5183-2085) was charged with 20 uL of methanol (LC/MS, JT Baker, Cat. 9863-01) containing 50 pg of each internal standard. The following internal standards from Cayman Chemicals were used ($d_4$-PGE$_2$, $d_4$-PGD$_2$, $d_4$-PGF$_{2\alpha}$, $d_4$-6-Keto-PGF$_{1\alpha}$, $d_4$-TXB$_2$, $d_8$-5(S)-HETE, $d_4$-LTB$_4$, $d_8$-arachidonic acid, stock solutions of internal standards in absolute ethanol were stored at −80° C. under Ar in Teflon septum, screw cap vials). To the vial was added the sample to be analyzed (i.e. 10 uL of serum). The vial insert was mixed on a vortex mixer for about 10 sec. The concentration of methanol was lowered to 10% (v/v) by addition of purified water (Milli-Q, Millipore Corp.), and the samples were loaded via a glass Pasteur pipette on to a solid phase extraction cartridge (either 30 mg Strata-X, Phenomenex Cat. 8B-S100-TAK-S or 10 mg Oasis-HLB, Waters Cat. 186000383). The cartridges were previously washed with 1 mL of methanol and then 2×0.75 mL 95/5 water/methanol. After sample loading, the sample tube was rinsed with 200 uL of purified water:methanol (95:5, v:v), and this was added to the cartridge.

The cartridge was washed with 2×1 mL water:methanol (95:5, v:v). Additional solvent was forced out of the cartridge solid phase by applying medium pressure $N_2$ (house $N_2$ passed through a 0.2 micron cartridge filter) for a few seconds. Column eluent receiver vials (Waters Total Recovery auto-sampler vials, Waters, Cat. 186002805) were placed under the cartridges. The cartridges were then eluted with methanol (1 mL). All cartridge steps were carried out using a vacuum manifold (Waters, Cat. WAT200606) attached to a water aspirator. Solvent was removed by placing the receiver vials in a centrifugal evaporator (Speed-Vac). These processed samples were derivatized with AMPP (see below) without storage.

Derivatization with AMPP.

To the residue in the Waters Total Recovery auto-sampler vial was added 10 uL of ice-cold acetonitrile (JT Baker, Cat. 9017-03):N,N-dimethylformamide (Sigma, Cat. 227056) (4:1, v:v). Then 10 uL of ice-cold 640 mM 3-(dimethylamino)propyl)ethyl carbodiimide hydrochloride (TCI America, Cat. D1601) in purified water was added. The vial was briefly mixed on a vortex mixer and placed on ice while other samples were processed as above. To each vial was added 20 uL of 5 mM N-hydroxybenzotriazole (Pierce, Cat. 24460)/15 mM AMPP in acetonitrile. The vials were mixed briefly on a vortex mixer, capped, and placed in a 60° C. incubator for 30 min. The cap was replaced with a split-septum screw cap for auto-injection onto the LC/ESI-MSMS (Agilent Cat. 5185-5824). Samples were analyzed on the same day. Samples were kept in the auto-sampler rack at 4° C. while queued for injection.

LC/ESI-MSMS Analysis.

Some studies were carried out with a Waters Quattro Micro triple quadrupole mass spectrometer, a 2795 Alliance HT LC/auto-sampler system and the QuanLynx software package. Chromatography was carried out with a C18 reverse-phase column (Ascentis Express C18, 2.1×150 mm, 2.7 um, Supelco Cat. 53825-U). Solvent A is 95% $H_2O$/5% $CH_3CN$/1% acetic acid, and solvent B is $CH_3CN$/1% acetic acid. The solvent program is (linear gradients): 0-1.0 min, 95-78% A; 1.0-7.0 min, 78-74% A; 7.0-7.1 min, 74-55% A; 7.1-12.1 min, 55-40% A; 12.1-13.0 min, 40-0% A; 13.0-15.0 min, 0% A; 15.0-15.1 min, 0-95% A; 15.1-20.1 min, 95% A. The flow rate is 0.25 mL/min.

Similarly, some studies were carried out with a Waters Quattro Premier triple quadrupole mass spectrometer interfaced to an Acquity HPLC. Solvent A is 100% water (Fisher Optima Grade Cat. L-13780)/0.1% formic acid (Fluke Cat. 94318), and solvent B is $CH_3CN$ (Fisher Optima Grade Cat. L-14338)/0.1% formic acid. The same LC column was used but with a modified solvent program (linear gradients): 0-1.0 min, 95% A; 1.0-2.0 min, 95%-85% A; 2.0-2.1 min, 85%-74% A; 2.1-6.0 min, 74%-71% A; 6.0-6.1 min, 71%-56% A; 6.1-10.0, 56% A, 10.0-14.0, 56%-0% A; 14.0-14.1, 0%-95% A; 14.1-18.0 min, 95% A.

Tables 5 and 6 give the auto-sampler and ESI-MSMS data collection parameters for the Waters Quattro Micro triple quadrupole and the Waters Quattro Premier triple quadrupole mass spectrometers, respectively.

For comparison purposes, LC/ESI-MSMS analysis of underivatized eicosanoids in negative ion mode was also carried out. The same LC column, solvent A and B, and flow rate was used as for the AMPP amides. The solvent program was slightly modified as follows. For the Waters Quattro Micro: 0-1.0 min, 95-63% A; 1.0-7.0 min, 63% A; 7.0-7.1 min, 63-38% A; 7.1-12.1 min, 38-23% A; 12.1-13.0 min, 23-0% A; 13.0-15.0 min, 0% A; 15.0-15.1 min, 0-95% A; 15.1-20.1 min, 95% A. For the Waters Quattro Premier: 0-1.0 min, 95% A; 1.0-2.0 min, 95%-85% A; 2.0-2.1 min, 85%-59% A; 2.1-6.0 min, 59% A; 6.0-6.1 min, 59%-38% A; 6.1-11, 38%-23% A, 11-11.1, 23%-0% A; 11.1-14, 0% A: 14.0-14.1, 0%-95% A; 14.1-19.0 min, 95% A. Values of m/z for parent and fragment ions were as published[5], and cone voltages and collision energies were optimized for each instrument and for each analyte.

Eicosanoid Recovery Studies.

The recovery of eicosanoids was measured following the sample workup procedure given above. Recovery studies were done with 50 pg or 5 pg of each eicosanoid in phosphate buffered saline. For these recovery studies, 50 pg of each internal standard was added to samples just prior to derivatization with AMPP (i.e. post-solid-phase extraction). Recoveries were obtained by comparing the LC/ESI-MSMS peak integrals to those obtained from a sample of eicosanoids that were derivatized with AMPP and injected directly onto the LC column without sample processing. Recovery yields are given in Table 1.

Limit of Quantification Determinations.

The limit of quantification of eicosanoid AMPP amides detected by LC/ESI-MSMS (defined as a signal-to-noise ratio for the analyte peak of 10 estimated using the MassLynx software) was measured. Limit of quantification values are summarized in Table 1 and are in the range of 5 pg for the primary prostanoids to 5-10 pg for HETEs and LTB$_4$. These are on the Waters Quattro Micro ESI-MSMS mass spectrometer. On the same instrument, limit of quantification values for non-derivatized eicosanoids measured by negative mode LC/ESI-MSMS analysis are in the range of 90-120 pg for the primary prostanoids and 80-200 pg for the HETEs and LTB$_4$. Thus, the detection sensitivity for AMPP amides is about 10- to 20-fold higher than that for negative mode detection of underivatized eicosanoids. On a newer model mass spectrometer (Waters Quattro Premier), the limits of quantification of eicosanoids are in the 200-1000 femtogram range (Table 1).

Studies with Primary Bronchial Epithelial Cells.

The University of Washington Institutional Review Board approved the studies involving human subjects, and written informed consent was obtained from all participants. Primary bronchial epithelial cells were isolated from a volunteer with asthma during bronchoscopy using a nylon cytology brush of cells from subsegmental airways. To establish primary culture, the epithelial cells were seeded into a culture vessel coated with type 1 collagen in bronchial epithelial basal media (BEBM, Lonza, Allendale, N.J.) supplemented with bovine pituitary extract, insulin, hydrocortisone, gentamicin, amphotericin B, fluconazole, retinoic acid, transferrin, triiodothyronine, epinephrine, and human recombinant epidermal growth factor (serum-free BEGM) and maintained at 37° C. in a humidified incubator. After expansion in vitro, passage 2 epithelial cells were grown to >90% confluence on a 12-well plate. The medium was changed to Hanks balanced salt solution, and the cells were treated with either calcium ionophore (A23187, 10 uM) or a DMSO-containing control solution for 20 min at 37° C. In some studies, the cytosolic phospholipase A$_2$-α inhibitor Pyr-2[6] was present at 5 uM, added from a stock solution in DMSO. The synthesis of eicosanoids was stopped by the addition of 4 volumes of ice methanol with 0.2% formic acid. The number of epithelial cells was 5.0×10$^5$ cells per well. The studies were performed in duplicate. Samples were processed for derivatization with AMPP and LC/ESI-MSMS as for the serum samples.

TABLE 1

Extraction yields, liquid chromatography retention times, and tandem mass spectrometry parameters for eicosanoid AMPP amide molecular species.

| Eicosanoid | Extr. yield (%)[1] | LC ret. time (min)[2] | Limit of quant. in pos. mode (pg)[3] | Limit of Quant. in neg. mode (pg)[4] | Parent ion[5] (m/z) | Fragment ion[5] (m/z) | Cone voltage[6] (V) | Collision energy[6] (eV) |
|---|---|---|---|---|---|---|---|---|
| 6-keto-PGF$_{1\alpha}$ | 102/87 | 5.4/4.1 | 5/0.3 | 110/10 | 537 | 239 | 65/80 | 55/55 |
| PGF$_{2\alpha}$ | 64/100 | 6.7/5.2 | 5/0.5 | 110/7 | 521 | 239 | 60/75 | 43/52 |
| PGE$_2$ | 67/74 | 6.8/5.3 | 5/0.3 | 100/7 | 519 | 239 | 60/75 | 40/45 |
| PGD$_2$ | 63/67 | 7.2/5.7 | 5/0.6 | 120/7 | 519 | 307 | 60/75 | 40/48 |
| TxB$_2$ | 86/86 | 6.2/4.6 | 5/0.2 | 90/4 | 537 | 337 | 65/70 | 43/42 |
| LTB$_4$ | 42/63 | 9.8/7.7 | 5/0.5 | 80/7 | 503 | 323 | 50/60 | 35/35 |
| 5(S)-HETE | 42/65 | 10.4/9.7 | 5/0.4 | 120/10 | 487 | 283 | 55/65 | 37/34 |
| 8(S)-HETE | 40/75 | 10.3/9.1 | 5/0.2 | 120/10 | 487 | 295 | 55/65 | 37/40 |
| 11(S)-HETE | 31/66 | 10.2/8.8 | 5/0.3 | 80/5 | 487 | 335 | 55/65 | 32/30 |
| 12(S)-HETE | 69/62 | 10.2/8.9 | 10/0.9 | 140/10 | 487 | 347 | 55/65 | 35/35 |
| 15(S)-HETE | 35/53 | 10.1/8.5 | 5/0.4 | 200/10 | 487 | 387 | 55/65 | 33/34 |
| Arachidonic acid | 73/113 | 11.7/12.4 | 10/1 | no data | 471 | 239 | 55/65 | 40/50 |
| d$_4$-6-keto-PGF$_{1\alpha}$ | | 4.05 | | | 541 | 241 | 50/75 | 43/52 |
| d$_4$-PGF$_{2\alpha}$ | | 5.14 | | | 525 | 241 | 65/80 | 55/55 |
| d$_4$-PGE$_2$ | | 5.25 | | | 523 | 241 | 60/75 | 40/45 |
| d$_4$-PGD$_2$ | | 5.61 | | | 523 | 311 | 60/75 | 40/48 |
| d$_4$-TxB$_2$ | | 4.57 | | | 541 | 341 | 65/70 | 43/42 |
| d$_4$-LTB$_4$ | | 7.74 | | | 507 | 325 | 50/60 | 35/35 |
| d$_8$-5(S)-HETE | | 9.61 | | | 495 | 284 | 55/65 | 37/34 |
| d$_8$-arachidonic acid | | 12.41 | | | 479 | 239 | 55/65 | 40/50 |

[1]The first number is for the Waters Oasis HLB cartridge, and the second number is for the Phenomenex Strata-X cartridge.
[2]The first number is for the Waters Quattro Micro, and the second number is for the Waters Quattro Premier.
[3]LOQ values are for eicosanoid AMPP amides in positive mode. The first number is for the Waters Quattro Micro, and the second number is for the Waters Quattro Premier.
[4]LOQ values are for underivatized eicosanoids analyzed by LC/ESI-MSMS in negative mode. The first number is for the Waters Quattro Micro, and the second number is for the Waters Quattro Premier.
[5]m/z Values listed are calculated monoisotopic values. The actual values used are derived from instrument tuning, which is instrument dependent.
[6]Cone voltages and collision energies were optimized for each analyte. These values are instrument dependent. The first value is for the Waters Quattro Micro instrument, and the second value is for the Waters Quattro Premier instrument.

TABLE 2

Coefficient of variation (%) for LC/ESI-MSMS analysis of eicosanoid AMPP amides.

| | Intra-sample[1] | Inter-sample (10 μL phosphate buffered saline)[2] | Inter-sample (10 μL serum)[3] |
|---|---|---|---|
| 6-keto-PGF$_{1\alpha}$ | 4.9 | 16.9 | not detected |
| TxB$_2$ | 2.4 | 3.0 | 3.7 |
| PGF$_{2\alpha}$ | 8.1 | 6.5 | 6.4 |
| PGE$_2$ | 8.0 | 9.2 | not detected |
| PGD$_2$ | 4.5 | 8.3 | not detected |
| LTB$_4$ | 7.3 | 17.2 | 7.3 |
| 5(S)-HETE | 3.3 | 2.8 | 6.4 |
| 8(S)-HETE | 6.7 | 20.3 | 13.7 |
| 11(S)-HETE | 5.5 | 12.2 | 8.8 |

TABLE 2-continued

Coefficient of variation (%) for LC/ESI-MSMS analysis of eicosanoid AMPP amides.

| | Intra-sample[1] | Inter-sample (10 μL phosphate buffered saline)[2] | Inter-sample (10 μL serum)[3] |
|---|---|---|---|
| 12(S)-HETE | 5.2 | 10.7 | 6.3 |
| 15(S)-HETE | 4.0 | 5.8 | 12.4 |
| Arachidonic acid | 12.7 | 28.2 | 7.9 |

[1]Coefficient of variation for the analysis of the same sample injected 3 times onto the LC/ESI-MSMS.
[2]Coefficient of variation for the analysis of 3 independent samples of eicosanoids spiked into phosphate buffered saline and worked up for LC/ESI-MSMS.
[3]Coefficient of variation for 3 separate serum samples spiked with internal standards only.

TABLE 3

Eicosanoid levels (pg) in mouse serum[1].

| Serum (μL) | $TxB_2$ | $PGF_{2\alpha}$ | $LTB_4$ | 5(S)-HETE | 8(S)-HETE | 11(S)-HETE | 12(S)-HETE | 15(S)-HETE | Arachidonic acid |
|---|---|---|---|---|---|---|---|---|---|
| 1 | 46 | 15 | 198 | 748 | 393 | 437 | 11345 | 240 | 28623 |
| 1 | 49 | 11 | 340 | 1075 | 545 | 646 | 17840 | 703 | 23246 |
| 5 | 214 | 64 | 869 | 3961 | 2452 | 1749 | 70578 | 3085 | 74500 |
| 5 | 213 | 53 | 846 | 4930 | 2344 | 1750 | 82562 | 3362 | 83156 |
| 10 | 513 | 89 | 2546 | 9705 | 5855 | 5364 | 151082 | 7493 | 122009 |
| 10 | 392 | 129 | 2480 | 9579 | 5931 | 4164 | 144874 | 7322 | 154769 |

[1]Eicosanoids not listed in the table were not detected.

TABLE 4

Eicosanoid levels (pg) from primary human bronchial cells.

| | Non-stimulated | +Ca ionophore | +Ca ionophore + pyr-2 (5 μM) |
|---|---|---|---|
| $TxB_2$ | 0.8 | 1.3 | 1.2 |
| $PGF_{2\alpha}$ | 34 | 60 | 43 |
| $PGE_2$ | 21 | 39 | 25 |
| $PGD_2$ | 4.9 | 4.4 | 5.0 |
| 11(S)-HETE | 1.0 | 3.7 | 3.8 |
| 15(S)-HETE | not detected | 7.8 | 4.9 |
| Arachidonic acid | 176 | 242 | 335 |

[1]Eicosanoids not listed in the table were not detected. Values are for 0.47 million cells per sample.

TABLE 5

Autosampler (2795 Alliance HT LC) and ESI-MSMS (Waters Quattro Micro) data collection parameters.

| Injection type | Sequential |
|---|---|
| Fill mode | Partial loop |
| Pre-sample air boundary | 2 μL |
| Post-sample air boundary | 2 μL |
| Post-injection wash frequency | 10 cycles |
| Flush time | 6 sec |
| Wash time | 15 sec |
| Secondary wash volume | 600 μL |

| | Negative Mode | Positive Mode |
|---|---|---|
| Capillary Voltage (kV) | (−) 2.8 | (+) 3.5 |
| Extractor (V) | 3 | 3 |
| RF Offset | 0.2 | 0.2 |
| Dwell Time (msec) | 50 | 50 |
| Inter-Scan Delay (msec) | 10 | 10 |
| Inter-Channel Delay (msec) | 100 | 100 |
| Source Temp (° C.) | 130 | 130 |
| Desolvation Temp (° C.) | 500 | 500 |
| Desolvation Gas (L/Hr) | 1100 | 1100 |
| Cone Gas (L/Hr) | 25 | 25 |
| Collision Cell Entrance (V) | −2 | −2 |
| Collision Cell Exit (V) | 1 | 1 |

TABLE 6

Autosampler (Water ACQUITY UPLC) and ESI-MSMS (Waters Quattro Premier) data collection parameters.

| Injection type | Sequential |
|---|---|
| Fill mode | Partial loop with needle overfill |
| Weak wash volume ($H_2O$) | 600 μL |
| Strong wash volume (50:50 ACN:MeOH) | 200 μL |
| Pre-Aspirate air gap | Automatic |
| Post-Aspirate air gap | Automatic |
| Syringe draw rate | Automatic |
| Needle placement | Automatic |

| | Negative Mode | Positive Mode |
|---|---|---|
| Capillary Voltage (kV) | −2.8 | +3.25 |
| Extractor (V) | 5 | 5 |
| RF Offset | 0.0 | 0.0 |
| Dwell Time (msec) | 50 | 50 |
| Inter-Scan Delay (msec) | 5 | 5 |
| Inter-Channel Delay (msec) | 10 | 10 |
| Source Temp (° C.) | 130 | 130 |
| Desolvation Temp (° C.) | 450 | 450 |
| Desolvation Gas (L/Hr) | 900 | 900 |
| Cone Gas (L/Hr) | 0 | 0 |
| Collision Cell Entrance (V) | −5 | −5 |
| Collision Cell Exit (V) | 0 | 0 |

While illustrative embodiments have been illustrated and described, it will be appreciated that various changes can be made therein without departing from the spirit and scope of the invention.

The invention claimed is:
1. A compound having the formula

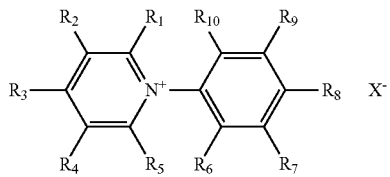

wherein $R_1$-$R_{10}$ are independently selected from hydrogen, an alkyl group, and -L-N(Z)H, wherein L is an alkylene, Z is hydrogen or an alkyl group including from one to twenty carbon atoms, provided that at least one of $R_1$-$R_{10}$ is -L-N(Z)H; and X⁻ is a counterion.

2. The compound of claim 1, wherein the compound is an N-(4-aminomethylphenyl)pyridinium (AMPP) salt.

3. The compound of claim 1, wherein Z is H.

4. The compound of claim 1, wherein L is methylene.

5. The compound of claim 1, wherein $R_1$-$R_7$, $R_9$, and $R_{10}$ are each hydrogen.

6. The compound of claim 1, wherein $R_8$ is -L-N(Z)H.

7. A kit for derivatizing a carboxylic acid, comprising:
   (a) a container comprising a compound of claim 1; and
   (b) indicia providing instructions for using the compound to derivatize a carboxylic acid.

8. The kit of claim 7, wherein the compound is an N-(4-aminomethylphenyl)pyridinium (AMPP) salt.

9. The kit of claim 7, wherein Z is H.

10. The kit of claim 7, wherein L is methylene.

11. The kit of claim 7, wherein $R_1$-$R_7$, $R_9$, and $R_{10}$ are each hydrogen.

12. A compound having the formula

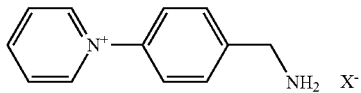

wherein X⁻ is a counterion.

* * * * *